United States Patent [19]

Gvaryahu

[11] Patent Number: 4,993,363

[45] Date of Patent: Feb. 19, 1991

[54] METHOD OF RAISING FARM ANIMALS BY EXPOSING THEM TO TOYS

[75] Inventor: Gadi Gvaryahu, Ithaca, N.Y.

[73] Assignee: Cornell Research Foundation, Inc., Ithaca, N.Y.

[21] Appl. No.: 217,977

[22] Filed: Jul. 12, 1988

[51] Int. Cl.$^5$ .............................................. A01K 15/02
[52] U.S. Cl. ........................................ 119/29; 119/5
[58] Field of Search ................. 119/5, 29, 64, 71, 134; D30/104, 105

[56] References Cited

U.S. PATENT DOCUMENTS

| | | | |
|---|---|---|---|
| 2,988,045 | 6/1961 | Fisher | 119/29 |
| 3,092,076 | 6/1963 | Novello | 119/29 X |
| 3,835,813 | 9/1974 | Katz | 119/5 |
| 4,802,444 | 2/1989 | Markham et al. | 119/29 |
| 4,825,812 | 5/1989 | Visalli et al. | 119/64 |

FOREIGN PATENT DOCUMENTS

| | | | |
|---|---|---|---|
| 78705 | 5/1986 | Israel . | |
| 2098041 | 11/1982 | United Kingdom | 119/5 |

OTHER PUBLICATIONS

Journal of Animal Science Abstracts, vol. 59, Supplement 1, Abstract Nos. 13 and 22.

Jones, R. B. et al., Growth and the Plasma Concentration of Growth Hormone and Prolactin in Chicks: Effects of "Environmental Enrichment", Sex and Strain, Poultry Science 21; 457–462 (1980).

Woody Gush, D. G. M. et al., The Enrichment of a Bare Environment for Animals in Confined Conditions, Applied Animal Ethology 10, 209–217 (1983).

Gvaryahu, et al., Application of the Filial Imprinting Phenomenon on Commercial Farm Broiler Chicks, (9/87).

*Primary Examiner*—Robert P. Swiatek
*Attorney, Agent, or Firm*—Jones, Tullar & Cooper

[57] ABSTRACT

A method of raising farm animals including mammals, birds, and fish, provides the farm animals with playing toys to improve their behavioral characteristics, feeding habits, mortality rates, and overall health and quality.

6 Claims, No Drawings

METHOD OF RAISING FARM ANIMALS BY EXPOSING THEM TO TOYS

BACKGROUND OF THE INVENTION

The present invention relates to a method for raising farm animals (mammals, birds, and fish) by exposing them to toys, and thereby improving their behavioral characteristics, feeding habits, and mortality rates.

Toys are objects which can be utilized by an animal for play. Play in animals has been described as "leaping; jumping; bucking or running when there is no obstacle to overcome, no enemy to flee, or object to obtain; sniffing; licking, pawing and manipulating familiar rather than novel objects; sex without coition; and, fighting in friendly rather than aggressive encounters which avoids injuring or routing the partner." (McFarland, 1981). According to McFarland, there are at least five categories of play activities:

1. Superfluous activity includes prancing, frisking, leaping, gambolling, etc., and has been in observed cattle, horses, sheep, goats, and chicks.

2. Aimless exploration, manipulating, and object play involves the use of novel stimuli and objects which typically elicit approach, touching, mouthing, and other manipulations, providing the animal is not frightened.

3. Practice play is often seen in animals whose movement is still not perfected at birth, and involves the repetition and elaboration of newly acquired and chance actions.

4. Responses to the wrong object are often found in young animals, and comprise innate sterotyped movements to inappropriate objects.

5. Finally, social play is play between young animals, and between the young and their parents. It has been suggested that social play may serve to establish dominance relationships, or to control aggression between group members.

Toys are the objects for animal play, and serve to stimulate other kinds of play or activity. Toys were developed and have been used for many years for pets (for cats, dogs, birds, and aquarium fish). Farm animals, unlike pets and wild animals, however, remain in poor and monotonic environments for the majority of their lives without any objects or toys to stimulate their senses. Since it appears that all animals require a certain amount of play type activity, it would appear to be beneficial to farm animals to enhance or enrich their playing environment. If such an enrichment to their playing environment results in improved behavioral characteristics, feeding habits, and mortality rates, for example, the derived economic benefit can be substantial, especially in a commercial farm environment where large numbers of animals are involved.

SUMMARY OF THE INVENTION

It is therefore the object of the present invention to provide a method for raising farm animals including mammals, birds, and fish, by providing the animals with toys for play, and thereby improving their behavioral characteristics, feeding habits, mortality rates, and overall health and quality.

This, and other objects of the invention, are achieved by exposing farm animals to different types of toys during their raising period. In a number of experiments, different types of farm animals were provided with various types of toys, and significant improvements in feeding habits, mortality rates, and overall health and behavior, were observed.

DETAILED DESCRIPTION OF THE PREFERRED EMBODIMENTS

Turning now to a more detailed consideration of the invention, in a first experiment, five hundred laying hens were provided with pecking toys. Aggressive pecking by laying hens and its relation to peck order and egg production is a well known issue. Researchers have attempted to reduce aggressive pecking of laying hens for many years in order to improve production. Beak trimming and polypeepers (plastic devices restricting forward vision) have been utilized for this purpose. The purpose then of pecking toys for laying hens is so chickens will peck or play more with those toys, and less with each other.

In the experiment, at five months of age, Leghorn chickens were exposed to a metal key ring with three beads and a jingle bell. The ring (one ring for every three chickens) was hung in the center of the cage and could easily be pecked by the hens. Good results were obtained with a ring three centimeters in diameter with red, blue, and green or yellow beads attached to it. Experiments using these toys have shown a consistent increase in egg production, and a steady decrease in feed use and mortality following seven months of production as illustrated in Table 1.

TABLE 1

|  | Egg Production (% hen-day) | Feed Usage Kg/bird | Mortality % |
|---|---|---|---|
| Control | 80.95 | 23.3 | 5.0 |
| Experimental | 81.70 | 23.0 | 3.0 |

In a second commercial experiment, 2000 laying hens were provided with pecking toys. A decrease in mortality (0.5 percent vs. 1%) and increase in egg production (2969 eggs vs. 2812 eggs (sum of 4 separate arbitrary egg countings)) resulted, following two months of production. Feed usage was not measured because of technical difficulties.

In the third and fourth experiments, fish were provided with environment enrichment toys. Environmental enrichment involves the increase of the stimulatory value of the home environment by increasing its complexity. In contrast to the many mammalian studies, very little is known about the effect of environmental enrichment on fish.

After being transferred from the hatchery, 600 Atlantic Salmon fish were exposed to marbles and plastic beads. This experiment had six replications. Good results were obtained with marbles and beads one centimeter in diameter, and in various colors. Experiments using these toys for four weeks have shown a significant ($P<0.01$) decrease in mortality as illustrated in Table 2. However, body weights of experimental fish were significantly reduced ($P<0.05$) unlike feed conversion.

TABLE 2

|  | Body weight (g) | Food:gain ratio | Mortality (%) |
|---|---|---|---|
| Control | 0.46 | 1.92 | 5 |
| Experimental | 0.43 | 1.89 | 1 |

The 4 percent differences in mortality in turn created differences in density which could explain the experimental fish's body weight reduction. For that reason, in the 6 replications of the fourth experiment, 450 Rainbow Trout were exposed to the same toys; this time, however with lower density. Four week long experiments have demonstrated (Table 3) that a significant ($p < 0.05$) decrease in mortality, an increase in body weight, and an improvement in food: gain ratio resulted when the toys were presented in the fish jars.

TABLE 3

|  | Body weight (g) | Food:gain ratio | Mortality (%) |
| --- | --- | --- | --- |
| Control | 0.93 | 1.71 | 5.3 |
| Experimental | 0.94 | 1.61 | 1.3 |

Finally, in a fifth experiment, lambs were provided with teething toys. A lamb, when born, may shown one or two temporary incisor teeth, or none at all. By the time the lamb is about two months old, it will have cut all eight temporary or milk incisors. Just like human babies, lambs will put things in their mouths and gnaw in order to relieve teething pain. It was therefore the purpose of this experiment to create teething toys for lambs.

In the experiment, four groups of lambs were exposed at one day of age to different kinds of rubber and metal toys. The toys were hung with metal chains from the ceiling of the cage and on the cage walls. Good results were obtained with wheel shaped rubber toys 10 cm. in diameter, horseshoe shaped rubber toys 10×5 cm., and metal screws 10×1 cm. Control lambs were raised under exactly the same conditions without the toys. Observations of both control and experimental lambs were made during their first three weeks of life. Experimental lambs approached, touched, and chewed the teething toys often during this period. The controls chewed the metal cage bars periodically, but this chewing behavior was not as frequent as with the experimentals.

As illustrated in Table 4, experiments using these toys have demonstrated that all four experimental groups (determined by different initial body weights) gained more weight on a percentage basis than did the controls. However, no differences in the morality rates were found. Also, feed usage was not recorded because of technical difficulties (lambs were fed from bottles).

TABLE 4

| Group Number | Initial Body Weight (at 6-12 hours of age) (Kg) | Number of lambs | Final Body Weight (3 weeks) (Kg) | % Gain |
| --- | --- | --- | --- | --- |
| 1. Experimental | 1.62 | (3) | 6.17 | 380.9 |
| Control | 1.71 | (3) | 6.30 | 368.4 |
| 2. Experimental | 2.16 | (4) | 7.02 | 352.0 |
| Control | 2.03 | (4) | 6.57 | 323.6 |
| 3. Experimental | 2.48 | (6) | 7.61 | 306.9 |
| Control | 2.57 | (6) | 7.70 | 299.6 |
| 4. Experimental | 2.88 | (8) | 8.24 | 286.1 |
| Control | 2.88 | (5) | 8.15 | 283.0 |

Although further experimentation needs to be conducted to better document the results, it is clear from these preliminary experiments, that exposure of farm animals, including mammals, birds, and fish, to toys, can significantly improve their behavior characteristics, feeding habits, mortality rates, and overall health and quality. As a result, the raising process becomes more efficient and commercially worthwhile.

Although the invention has been disclosed in terms of specific examples, it will be understood that numerous variations and modifications could be made without departing from the true spirit and scope of the inventive concept as set forth in the following claims.

What is claimed is:

1. A method for raising commercial farm fish comprising the step of:

providing commercial farm fish with one or more toys that stimulate play to reduce the mortality rates and increase the body weights of said commercial farm fish.

2. The method of claim 1 wherein the step of providing commercial farm fish with one or more toys that stimulate play comprises providing commercial farm fish with marbles or beads.

3. The method of claim 1 wherein the step of providing commercial farm fish with one or more toys that stimulate play comprises providing Salmon with one or more toys that stimulate play.

4. The method of claim 1 wherein the step of providing commercial farm fish with one or more toys that stimulate play comprises providing Rainbow Trout with one or more toys that stimulate play.

5. A method of raising commercial mature laying hens comprising the step of:

providing commercial mature laying hens with one or more toys that stimulate play to reduce mortality rates and increase egg production of said commercial mature laying hens.

6. The method of claim 5 wherein the step of providing commercial mature hens with one or more toys that stimulate play comprises providing commercial mature laying hens with one or more pecking toys that stimulate play.

* * * * *